(12) United States Patent
Ju et al.

(10) Patent No.: US 7,932,359 B2
(45) Date of Patent: Apr. 26, 2011

(54) ANTI-CAVEOLIN-1 POLYCLONAL ANTIBODY, AND ANTIGEN PEPTIDE SEQUENCE AND METHOD FOR PREPARING THE SAME

(75) Inventors: Yu-Ten Ju, Taipei (TW); Jih-Tay Hsu, Taipei (TW); Yan-Nian Jiang, Taipei (TW); Meng-Wei Ke, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/081,520

(22) Filed: Apr. 17, 2008

(65) Prior Publication Data

US 2009/0130132 A1    May 21, 2009

(30) Foreign Application Priority Data

Nov. 15, 2007   (TW) ............................. 96143320 A

(51) Int. Cl.
*C07K 16/00* (2006.01)
(52) U.S. Cl. ................ 530/387.1; 530/389.1; 530/391.3
(58) Field of Classification Search .......................... None
See application file for complete search history.

(56) References Cited

U.S. PATENT DOCUMENTS 5,744,585 A * 4/1998 Medenica et al. ....... 530/388.15

OTHER PUBLICATIONS

Hurlstone et al Oncogene, vol. 18, p. 1881-1890, 1999.*
Fukimoto et al J. cell Sci. vol. 113, p. 3509-3517, 2000.*
Data sheet, BD transduction lab 13630-610059, copy right 2007-2010.*
Data sheet, Santa Cruz SC-884,copy right 2007-2010.*
Scherer et al J Bio Chem vol. 270, p. 16395-16401, 1995.*
Sequence search result-1, 2009.*
Sequence search result-2, 2009.*

* cited by examiner

*Primary Examiner* — Misook Yu
*Assistant Examiner* — Lei Yao
(74) *Attorney, Agent, or Firm* — Bacon & Thomas, PLLC

(57) ABSTRACT

The present invention provides a highly specific anti-Caveolin-1 polyclonal antibody, which is prepared by the following steps: (1) providing an antigen comprising a fragment of Caveolin-1 peptide sequence SEQ ID NO: 1; and (2) subcutaneously injecting said antigen into a rabbit to produce the anti-Caveolin-1 polyclonal antibody. The present invention also provides an antigen and a method used for preparing the anti-Caveolin-1 polyclonal antibody, and a kit used for detecting Caveolin-1 in a specimen.

17 Claims, 6 Drawing Sheets

A

B

US 7,932,359 B2

ANTI-CAVEOLIN-1 POLYCLONAL ANTIBODY, AND ANTIGEN PEPTIDE SEQUENCE AND METHOD FOR PREPARING THE SAME

BACKGROUND OF THE INVENTION

1. Field of the Invention

The present invention relates to a highly specific anti-Caveolin-1 polyclonal antibody, an antigen and a method used for preparing said antibody, and a kit used for detecting Caveolin-1 in a specimen.

2. Description of the Related Art

Caveolin-1 is a 21-24 kDa membrane protein containing 178 amino acid residues, and it is abundant in caveolaes. Caveolaes are invaginations of the plasma membrane, and cholesterol and signal transducing molecules are accumulated in these invaginations. Both N- and C-terminal domains of Caveolin-1 are hydrophilic and oriented toward the cytoplasm, while the hydrophobic central stretch is embedded in the membrane. The N-terminal region of Caveolin-1 (amino acid residues 82-101) is necessary for its interaction with signal transducing molecules, while the C-terminal region (amino acid residues 135-178) is essential for Caveolin-1 dimer formation from its monomers, and for the membrane attachment of Caveolin-1. Caveolin-1 expression in mammals is down-regulated during late pregnancy and lactation through a prolactin signaling cascade. Overexpression of recombinant Caveolin-1 in mammary epithelial cell line HC11 inhibits the β-casein expression induced by prolactin. In addition, mammary gland development in Caveolin-1 null mice is earlier than in normal mice (Park et al., 2001). Therefore, Caveolin-1 acts as a negative regulator during mammary development and lactation. If Caveolin-1 expression in medium and large lactating animals can be detected, it may be helpful to study the role played by Caveolin-1 in the mammary gland.

In pathology studies, it has been found that Caveolin-1 expression is lost or down-regulated in many tumorous tissues of, for example, breast, ovary, prostate and colon cancers, and Caveolin-1 is regarded as an indicator for the progression of these cancers (Sloan et al., 2004; Wikman et al., 2004). Another prior study has found, using mRNA subtractive hybridization, that there is an obvious difference between Caveolin-1 gene expression in normal and tumorous human mammary epithelial cells (Sager et al., 1994). Another study found that Caveolin-1 expression in mammary adenocarcinoma-derived cells was much lower than in normal mammary epithelial cells. When Caveolin-1 was overexpressed in tumor cell lines, cell tumorigenesis was suppressed (Park et al., 2001). Ectopic expression of recombinant Caveolin-1 in mammary adenocarcinoma cells through cell transfection reduced the metastatic potential of these cells (Zhang et al., 2000). These studies have demonstrated that Caveolin-1 is anti-tumorigenic and can be used as a molecular indicator to diagnose the progression of some cancers.

The current method of detection of Caveolin-1 protein in tissues and cells is by immunochemical or immunofluorescent staining, and there are dozens of commercial anti-Caveolin-1 antibodies in the market. However, most of these commercial anti-Caveolin-1 antibodies are produced by the antigen derived from N-terminal amino acid residues 1-20 or 30-44 of Caveolin-1, and some of them are produced by the antigen derived from C-terminal of Caveolin-1. Bush et al. (2006) used five different anti-Caveolin-1 antibodies (developed by other teams) to detect the location of expressed Caveolin-1 in MDCK cells, and found that the specific locations of Caveolin-1 detected by different antibodies were different. This finding indicates that different anti-Caveolin-1 antibodies vary in their ability to label Caveolin-1 in cells, and the Caveolin-1 signals detected by these antibodies show different patterns.

Therefore, an anti-Caveolin-1 antibody with a higher efficiency to Caveolin-1 will be extremely advantageous for cancer research and the development of cancer treatments.

SUMMARY OF THE INVENTION

To solve the above-mentioned problems, one objective of the present invention is to provide an anti-Caveolin-1 polyclonal antibody, which is prepared by the following steps: (1) providing an antigen comprising a fragment of Caveolin-1 peptide sequence SEQ ID NO: 1; and (2) subcutaneously injecting said antigen into a rabbit to produce the anti-Caveolin-1 polyclonal antibody. Said anti-Caveolin-1 polyclonal antibody recognizes Caveolin-1 of a variety of mammalian species, and it can be used to monitor the progression of a variety of cancers.

Another objective of the present invention is to provide a method for preparing the above-mentioned anti-Caveolin-1 polyclonal antibody.

A further objective of the present invention is to provide a peptide sequence for preparing the above-mentioned anti-Caveolin-1 polyclonal antibody.

Yet another objective of the present invention is to provide a kit for the detection of Caveolin-1 in a specimen, comprising the above-mentioned anti-Caveolin-1 polyclonal antibody, and this kit may further comprise a secondary antibody having a signal; in addition, this kit can be used for detecting Caveolin-1 in a variety of mammalian species and monitoring the progression of a variety of cancers.

To achieve these objectives, the present invention provides an anti-Caveolin-1 polyclonal antibody, which is prepared by the following steps:

(1) providing an antigen comprising a fragment of Caveolin-1 peptide sequence SEQ ID NO: 1; and
(2) subcutaneously injecting said antigen into a rabbit to produce the anti-Caveolin-1 polyclonal antibody.

In preferred embodiments of the present invention, said antigen is listed in the sequence listing as SEQ ID NO: 2 and is of the following formula:

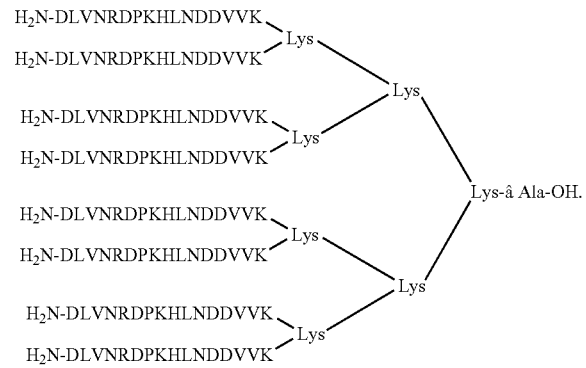

In preferred embodiments of the present invention, said anti-Caveolin-1 polyclonal antibody recognizes Caveolin-1 of mammals; more preferably, recognizes Caveolin-1 of human, cattle, goat, rat or mouse; and most preferably, recognizes Caveolin-1 of human, goat or mouse.

In preferred embodiments of the present invention, said anti-Caveolin-1 polyclonal antibody is used as a cancer indicator for monitoring cancer progression; more preferably, for monitoring breast or colon cancer progression.

The present invention also provides a method for preparing an anti-Caveolin-1 polyclonal antibody, comprising the following steps:
(1) providing an antigen comprising a fragment of Caveolin-1 peptide sequence SEQ ID NO: 1; and
(2) subcutaneously injecting said antigen into a rabbit to produce the anti-Caveolin-1 polyclonal antibody.

In preferred embodiments of the present invention, said antigen is listed in the sequence listing as SEQ ID NO: 2 and is of the following formula:

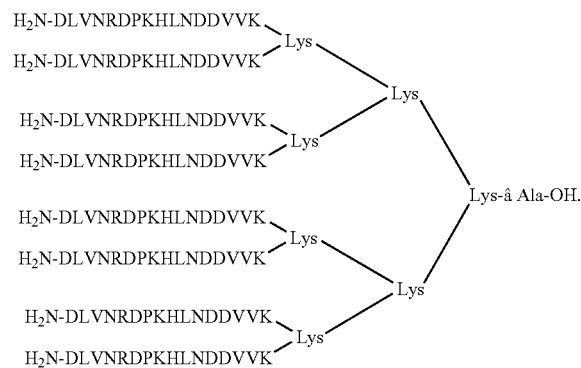

The present invention also provides an antigen for preparing the anti-Caveolin-1 polyclonal antibody according to claim 1, comprising a fragment of Caveolin-1 peptide sequence SEQ ID NO: 1.

In preferred embodiments of the present invention, said antigen is listed in the sequence listing as SEQ ID NO: 2 and is of the following formula:

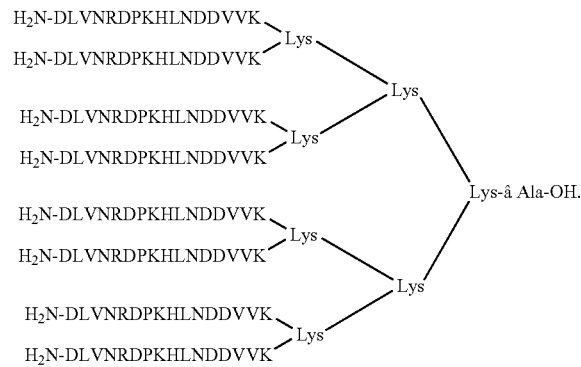

In addition, the present invention provides a kit used for detecting Caveolin-1 in a specimen, comprising the above-mentioned anti-Caveolin-1 polyclonal antibody.

In preferred embodiments of the present invention, said kit further comprises a secondary antibody having a signal; more preferably, said signal is fluorescence- or enzyme-generated; and most preferably, said enzyme is horseradish peroxidase (HRP), and said fluorescence is FITC or Texas-Red.

In preferred embodiments of the present invention, said specimen is a tissue section or a cell sample; more preferably, said tissue section is a cancer tissue section; even more preferably, said cancer tissue section is a breast cancer or colon cancer tissue section; and most preferably, said cancer tissue section is a human breast cancer or colon cancer tissue section.

In preferred embodiments of the present invention, said specimen is obtained from human, cattle, goat, rat or mouse; more preferably, from human, goat or mouse.

In preferred embodiments of the present invention, said kit is used for detecting Caveolin-1 in a cancer tissue specimen; more preferably, for detecting Caveolin-1 in a breast or colon cancer tissue specimen.

Additionally, the present invention provides an anti-Caveolin-1 polyclonal antibody, which binds to Caveolin-1, and not to Caveolin-2 or Caveolin-3; more preferably, said Caveolin-1, Caveolin-2 or Caveolin-3 is obtained from human, cattle, goat, rat or mouse.

In summary, the present invention provides an anti-Caveolin-1 polyclonal antibody, which is a rabbit polyclonal antibody obtained by using the peptide sequence composed of N-terminal amino acid residues 50-65 of Caveolin-1 as an antigen. Said peptide sequence has a high hydrophilicity and a high immunogenicity, and it is highly conserved in the peptide sequence of Caveolin-1 in many species, such like human, monkey, orangutan, cattle, goat/sheep, horse, muntjac, dog, cat, rat, mouse, and the like. Therefore, the antibody of the present invention can broadly recognize Caveolin-1 in cells or tissues obtained from a variety of species, such as human, cattle, goat, rat, mouse, and the like. In addition, the anti-Caveolin-1 polyclonal antibody of the present invention can recognize and distinguish the expression difference of Caveolin-1 in normal and tumorous tissues from colon or breast, so it can be used as a cancer indicator for detecting the tumorigenesis and progression of tumors, and brings a great benefit to the related cancer researches.

DETAILED DESCRIPTION OF THE PREFERRED EMBODIMENTS

After a long process of research and development, the applicants designed an antigen comprising a fragment of Caveolin-1 peptide sequence SEQ ID NO: 1, and subcutaneously injected said antigen into a rabbit to produce the anti-Caveolin-1 polyclonal antibody. Said anti-Caveolin-1 polyclonal antibody recognizes Caveolin-1 of a variety of mammalian species, and it can be used as a cancer indicator to monitor the progression of a variety of cancers. Details of the operation and technical features of the present invention are demonstrated in the following examples in coordination with the drawings. These examples, however, are used to further illustrate the advantages of the present invention, not to limit the scope claimed in this invention.

Examples

The Preparation of the Antigen

A fragment of peptide sequence was selected from the peptide sequence of human Caveolin-1 (GenBank, Hs. 74034; NP_001744) by DNA Star software (DNASTAR, Inc.). Said fragment is composed of the amino acid residues 50-65 of human Caveolin-1, that is, DLVNRDPKHLND-DVVK (SEQ ID NO: 1). This fragment, which is different from other binding sites for proteins known to interact with Caveolin-1, is located on the cell surface, and it has a high hydrophilicity and a high immunogenicity. Additionally, the sequences of Caveolin-1 of at least 16 species were searched in the NCBI (National Center for Biotechnology Information) database. These sequences were aligned by DNA Star software, and we found that the amino acid residues 50-65 of Caveolin-1 are a consensus sequence, which is highly conserved in many species, such as human, monkey, orangutan, cattle, goat/sheep, horse, muntjac, dog, cat, rat, mouse, and the like.

Figure 1:
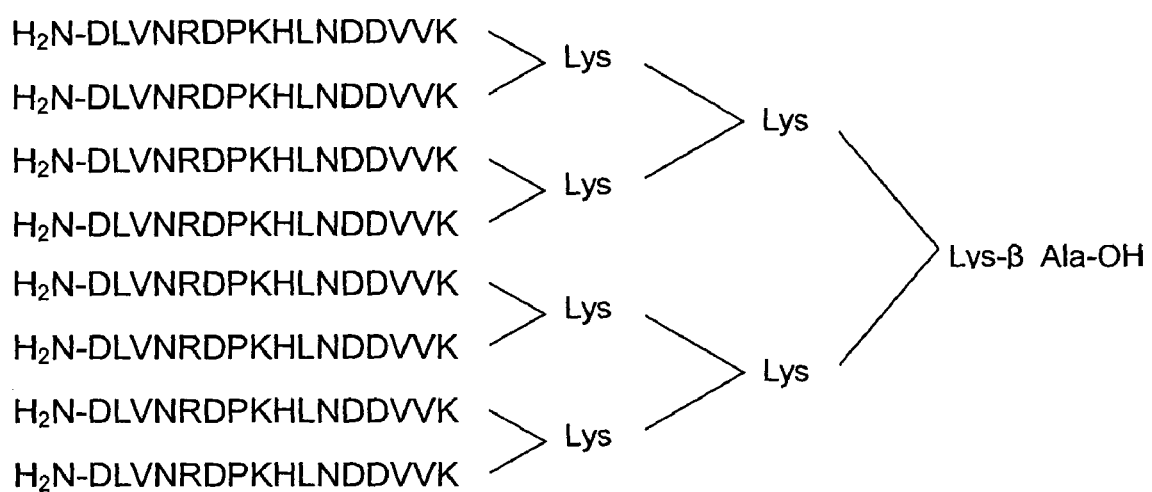
FIG. 1 shows the structure of the Caveolin-1 antigen (SEQ ID NO: 2) of the present invention.

A peptide sequence comprising said SEQ ID NO: 1 was synthesized and modified to the Caveolin-1 antigen as below (SEQ ID NO: 2) by multiple antigen peptide system, and the structure of said antigen is shown in FIG. 1:

[(H$_2$N-(DLVNRDPKHLNDDVVK))$_2$-Lys]$_4$-Lys$_2$-Lys-βAla-OH

Preparation of Polyclonal Antibody 1.5 kg New Zealand semi-lop white rabbits were selected to generate the antibody of the present invention. The pre-immune rabbit sera were collected; subsequently, 1.0 mg of the antigen and Freund's complete adjuvant (Sigma-Aldrich Fine Chemical, Inc.) were mixed and injected subcutaneously into the rabbits to induce a primary immune response. Four weeks later, 0.5 mg of the antigen and Freund's incomplete adjuvant (Sigma-Aldrich Fine Chemical, Inc.) were mixed and injected subcutaneously into the rabbits as the first booster. These rabbits were boosted every four weeks for a total of three boosters, and then bled to obtain the immune serum comprising the polyclonal antibody of the present invention from the third week after the second booster. All experiments hereinafter were performed with the immune serum comprising the polyclonal antibody obtained after the third booster.

Plasmid Construction

The full-length cDNA of Caveolin-1 obtained from an adult C57BL/6J mouse was amplified by RT-PCR (forward primer: CTCGAGATGTCTGGGGGCAAATACGTG (SEQ ID NO: 3); reverse primer: TCTAGATATCTCTTTCTGCGT-GCTGATGCG (SEQ ID NO: 4)). The obtained PCR product was cloned into pGEM-T easy vector (Promega Inc. USA), and then subcloned into pcDNA4/myc-His A vector (Invitrogen Inc., USA) through restriction enzyme digestion to obtain a pcDNA4-Caveolin-1 construct, wherein the C-terminal of Caveolin-1 was Myc-tagged.

The full-length cDNA of Caveolin-2 obtained from the mammary gland of an ICR mouse on lactation day 15 was amplified by RT-PCR (forward primer: GAATTCGGTAC-CATGGGGCTGGAGACCGAGAAGGC (SEQ ID NO: 5); reverse primer: AAGCTTTCTAGAGTCGTGGCTCAGT-TGCATGC (SEQ. ID NO: 6)). The obtained PCR product was cloned into pGEM-T Easy Vector, and then subcloned into pcDNA4/Myc-His A vector through restriction enzyme digestion to obtain a pcDNA4-Caveolin-2 construct.

In addition, the full-length cDNA of Caveolin-3 obtained from the muscle of an ICR mouse was amplified by RT-PCR (forward primer: CGGCAGCGGCACGAGTC (SEQ. ID NO: 7); reverse primer: CTCCCGCACCAAGTTTTC-CCATCT (SEQ. ID NO: 8)). The obtained cDNA was amplified by nested PCR (forward primer: GGATCCCTCGAGAT-GATGACCGAAGAGCACACGG (SEQ. ID NO: 9); reverse primer AAGCTTTCTAGAGCCTTCCCTTCGCAG-CACCACC (SEQ. ID NO: 10)). Later, the final PCR product was cloned into pcDNA4/Myc-His A vector through restriction enzyme digestion to obtain a pcDNA4-Caveolin-3 construct.

Cell Culture

All cell lines mentioned in this specification were purchased from American Type Culture Collection (ATCC). Mouse fibroblast cell line NIH 3T3 (ATCC CRL-1658) and human epithelial cell line A431 (ATCC CRL 1555) were cultured in Dulbecco's Modified Eagle's Medium supplemented with 10% fetal bovine serum, 2 mM L-glutamine, 100 U/mL of both penicillin and streptomycin; human mammary epithelial cell line MCF-7 (ATCC HTB-22) was cultured in α-MEM medium supplemented with 10% fetal bovine serum, 2 mM L-glutamine, 100 U/mL of both penicillin and streptomycin; and rat pituitary adenoma cell line GH3 (ATCC CCL-82.1) was cultured in F12K nutrient mix medium supplemented with 2.5% fetal bovine serum, 15% horse serum, 2 mM L-glutamine, 100 U/mL of both penicillin and streptomycin. The above-mentioned media, sera, L-glutamine and antibiotics were purchased from Life Technologies (Gaithersburg, Md., USA). In addition, goat mammary epithelial primary cells (GMEC) were maintained in MCDB 171 medium supplemented with Mammary Epithelial Growth Supplement (MEGS; Cascade Biologics Com.). The mouse muscles were removed directly from the mouse body, immersed in RIPA buffer [50 mM Tris-HCl (pH 7.0), 1% NP-40, 0.25% sodium deoxycholate, 150 mM NaCl, 1 mM PMSF, 56 µg/mL aprotinin, 10 µg/mL leupeptin, 1 µg/mL pepstatin, 1 mM $Na_3VO_4$, 1 mM NaF, 10 mM $Na_4P_2O_7$], and homogenized for 2 minutes at 20,000 rpm and 4° C. by a homogenizer (Model 212 Type II). Subsequently, the homogenized product was kept on ice for 20 minutes and then centrifuged at 14,000 rpm for 5 minutes by a centrifuge (KUBOTA1700). The upper liquid layer from centrifugation is the main source of Caveolin-3.

Cell Transfection

The rat pituitary adenoma cell line GH3 (FIG. 2B) and human mammary epithelial cell line MCF-7 (FIG. 3) were transfected by using Lipofectamine Plus™ Reagent kit (Life Technologies). First, $3 \times 10^5$ cells were seeded in a 35 mm Petri dish and incubated overnight. 1 µg DNA to be transfected and 6 µL Plus™ reagent were mixed, diluted to 100 µL by serum-free medium, then mixed with 4 µL Lipofectamine and kept at room temperature for 15 minutes to let DNA, Plus™ and Lipofectamine form a complex. Next, the DNA-Plus™-Lipofectamine complex was mixed with 800 µL serum-free medium, added into the Petri dish, and incubated in an incubator (37° C., 5% $CO_2$) for 3 hours. After that, the serum-free medium was replaced with fresh complete medium, and incubated in the incubator (37° C., 5% $CO_2$) for a further 48 hours.

After 48 hours, the total protein contents of the cells were extracted, quantified by Bio-Rad protein assay kit (Bio-Rad, Hercules, Calif.), and then subjected to a protein analysis by Western blotting.

Antibody Titer Assayed by Dot Blotting

Figure 2:
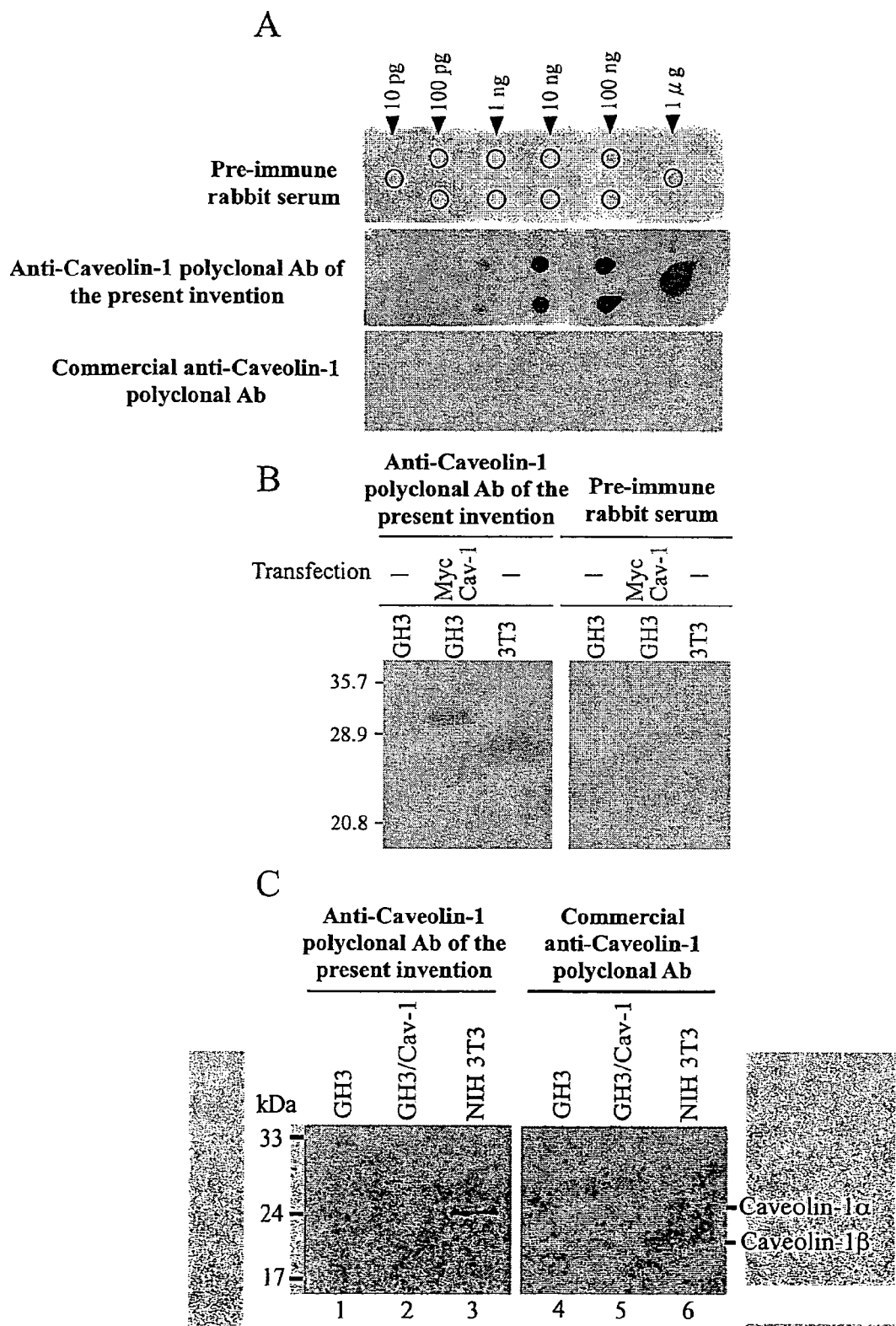
FIG. 2 demonstrates that the anti-Caveolin-1 polyclonal antibody of the present invention recognizes the Caveolin-1 antigen of the present invention, and this recognition is better than that of the commercial anti-Caveolin-1 polyclonal antibody (panel A); in addition, the anti-Caveolin-1 polyclonal antibody of the present invention recognizes the exogenous Caveolin-1 transfected into GH3 cells and the endogenous Caveolin-1 in NIH 3T3 cells (panel B), and has a better titer than the commercial anti-Caveolin-1 polyclonal antibody (panel C). Pre-immune rabbit serum is used as negative control.
Figure 3:
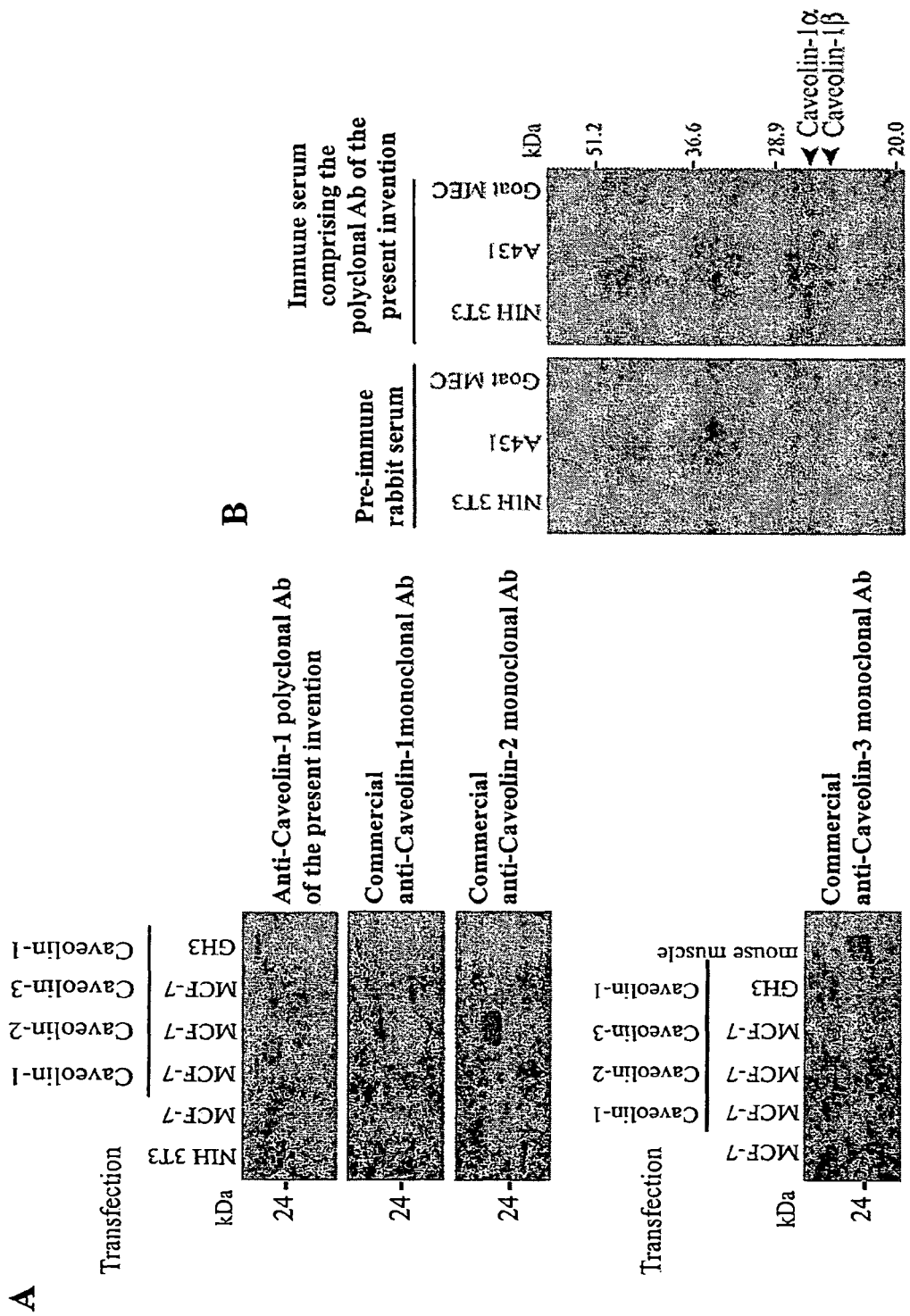
FIG. 3A demonstrates that the anti-Caveolin-1 polyclonal antibody of the present invention specifically recognizes Caveolin-1, while no signal is generated by Caveolin-2 or Caveolin-3. The anti-Caveolin-1 polyclonal antibody of the present invention and commercial anti-Caveolin-1, Caveolin-2 or Caveolin-3 monoclonal antibodies are used to examine Caveolin-1, Caveolin-2 or Caveolin-3 transfected MCF-7 cells by Western blotting, wherein NIH 3T3 cells are used as positive control of Caveolin-1 and Caveolin-2, mouse muscles are used as a positive control for Caveolin-3, and un-transfected MCF-7 cells are used as a negative control.
FIG. 3B demonstrates that, in mouse NIH 3T3 cells, human A431 cells, and goat GMEC cells, the anti-Caveolin-1 polyclonal antibody of the present invention is capable of cross-species detection. Pre-immune rabbit serum is used as a negative control.

As shown in FIG. 2A, the antibody titers were determined by dot blotting. First, the Caveolin-1 antigen was serially diluted by deionized water, and the final concentration was adjusted to 10 pg, 100 pg, 1 ng, 10 ng, 100 ng and 1 µg of Caveolin-1 antigen per 1 µL solution. The antigen solution of each concentration was spotted on nitrocellulose membrane. After these dots were dried, the membrane was blocked by 5% skimmed milk powder (Anchor) in TBST buffer at room temperature for 1 hour. The nitrocellulose membrane was then rinsed in TBST buffer 3 times, each time for 5 minutes. After that, the immune serum comprising the polyclonal antibody of the present invention was diluted by TBST buffer at a variety of ratios, and allowed to react with the antigen on the nitrocellulose membrane at 4° C. for 12 hours. Pre-immune rabbit serum was used as a negative control, and a commercial antibody was used as a positive control. Finally, the membrane was developed with ECL and exposed onto an X-ray film. FIG. 2A shows that a 1:10,000 dilution of the immune serum comprising the polyclonal antibody was able to detect the Caveolin-1 antigen at the level of 10 pg which means the polyclonal antibody has an extremely high sensitivity.

Extraction of Protein Samples

Transfected or untransfected cells were harvested by adding of RIPA buffer [50 mM Tris-HCl (pH 7.0), 1% NP-40, 0.25% sodium deoxycholate, 150 mM NaCl, 1 mM PMSF, 56 µg/mL aprotinin, 10 µg/mL leupeptin, 1 µg/mL pepstatin, 1 mM $Na_3VO_4$, 1 mM NaF, 10 mM $Na_4P_2O_7$] and the harvested cells were centrifuged at 12,000 rpm (15,000 g) for 10 minutes at 4° C. to obtain the total protein in the supernatant. The above-mentioned cells comprised: GH3 cells expressing no Caveolin-1 (negative control); GH3 cells transfected with Myc-tagged pcDNA4-Caveolin-1 construct (positive control); MCF-7 cells transfected with pcDNA4-Caveolin-1, pcDNA4-Caveolin-2 or pcDNA4-Caveolin-3; NIH 3T3 cells expressing a large amount of Caveolin-1 (positive control); mouse muscles (positive control); and human epithelial cell line A431 and goat mammary epithelial primary cells (GMEC).

Protein Analysis by Western Blotting

The total protein solutions obtained from each of the above-mentioned cells were quantified. As for those total protein solutions to be analyzed, aliquots of 20 µg protein were taken, mixed with 1× Laemmli buffer [2% SDS, 10% glycerol, 100 mM DTT, 60 mM Tris-HCl (pH6.8) and 0.01% bromophenol blue], heated at 95° C. for 5 minutes to denature the protein, and then loaded onto a 10-15% gradient gel and separated by SDS-PAGE protein gel electrophoresis in 1× protein electrophoresis buffer [25 mM Tris-HCl (pH 8.3), 192 mM glycine, 20% methanol]. After the electrophoretic separation, the proteins in the gel were transferred onto PVDF membrane in 1× wet transfer buffer [25 mM Tris-HCl, 190 mM glycine, 20% methanol], then the PVDF membrane was soaked in amido black staining solution (0.1% amido black, 40% methanol and 10% acetic acid in deionized water) for 5 minutes to check the transfer efficiency and the protein positions marked thereon, then the membrane was destained by immersion in the destaining solution (40% methanol and 10% acetic acid in deionized water) for 3 times, each time for 5 minutes. Subsequently, the PVDF membrane was washed in deionized water until no oily substance remained on the surface of the membrane. The membrane was blocked in 50 mL blocking solution (5% skimmed milk powder (Anchor) in TBST buffer [20 mM Tris-HCl (pH 7.5), 150 mM NaCl, 0.05% Tween-20]) at room temperature for 1.5 hours, and then washed in TBST buffer. A 1:3,000 dilution of primary antibody described hereinafter in TBST buffer was applied to the PVDF membrane and allowed to react at 4° C. for 12 hours, and then the membrane was washed in TBST buffer for three times. Later, a 1:3,000 dilution of HRP-conjugated anti-rabbit IgG antibody (Amersham Biosciences) in TBST buffer was added to the PVDF membrane as a secondary antibody and allowed to react at room temperature for 2 hours under constant rotational agitation, and then the membrane was washed in TBST buffer three times. Finally, ECL reagents (Amersham Biosciences) were added to develop signals, and the signals were exposed onto an X-ray film.

a. Antibody Sensitivity Test by Western Blotting

Protein electrophoresis by SDS-PAGE was performed in 12% polyacrylamide gels according to the above-mentioned procedure using protein samples obtained from GH3 cells transfected with Myc-tagged pcDNA4-Caveolin-1 construct, GH3 cells (negative control) and NIH 3T3 cells (positive control). Western blotting analysis was performed by using the pre-immune rabbit serum and the immune serum comprising the polyclonal antibody of the present invention as the primary antibodies, and using the HRP-conjugated anti-rabbit IgG antibody as the secondary antibody. These results are shown in FIG. 2B. Additionally, the above-mentioned protein samples were loaded onto 10% polyacrylamide gels and separated by SDS-PAGE as above. Subsequently, another Western blotting analysis was performed by using the immune serum comprising the polyclonal antibody of the present invention and a rabbit polyclonal antibody against N-terminal amino acid residues 1-105 of human Caveolin-1 (Chemicon International Inc.) as the primary antibodies, and using the HRP-conjugated anti-rabbit IgG antibody as the secondary antibody. These results are shown in FIG. 2C, in which the X-ray film obtained by using the immune serum comprising the polyclonal antibody of the present invention as the primary antibody was exposed about 5 seconds, and the X-ray film obtained by using the commercial antibody as the primary antibody was exposed about 5 minutes. From the results shown in FIGS. 2B and 2C, it is known that the polyclonal antibody of the present invention not only recognizes the artificially synthesized Caveolin-1, but also recognizes the endogenous Caveolin-1, including Caveolin-1α and Caveolin-1β, in NIH 3T3 cells; also, it has a higher sensitivity than the commercial antibody.

b. Antibody Specificity Test by Western Blotting

Also, protein electrophoresis was performed by protein samples obtained from MCF-7 cells transfected by pcDNA4-Caveolin-1, pcDNA4-Caveolin-2 or pcDNA4-Caveolin-3, GH3 cells transfected with myc-tagged pcDNA4-Caveolin-1 construct, MCF-7 cells (negative control), and NIH 3T3 cells and mouse muscles (positive control). Western blotting analysis was performed by using the immune serum comprising the polyclonal antibody of the present invention, and commercial Caveolin-1 monoclonal antibody (clone 2297), Caveolin-2 monoclonal antibody (clone 65) and Caveolin-3 monoclonal antibody (clone 26) (purchased from BD Biosciences) as the primary antibodies, and using the HRP-conjugated anti-rabbit IgG antibody as the secondary antibody. The results are shown in FIG. 3A. From these results, it is known that the polyclonal antibody of the present invention is specific to Caveolin-1, and it does not cross-react with Caveolin-2 or Caveolin-3.

c. Cross-Species Analysis by Western Blotting

Protein electrophoresis by SDS-PAGE was performed in 10% polyacrylamide gels according to the above-mentioned procedure using protein samples obtained from mouse NIH 3T3 cells, human A431 cells and goat GMEC cells. Western blotting analysis was performed by using the pre-immune rabbit serum (negative control) and the immune serum comprising the polyclonal antibody of the present invention as the primary antibodies, and using the HRP-conjugated anti-rabbit IgG antibody as the secondary antibody. The results are shown in FIG. 3B. From these results, it is known that the polyclonal antibody of the present invention recognizes Caveolin-1 of a variety of species and can be used in a cross-species analysis.

Detection of Endogenous Caveolin-1 in Cells by Immunostaining

Figure 4:
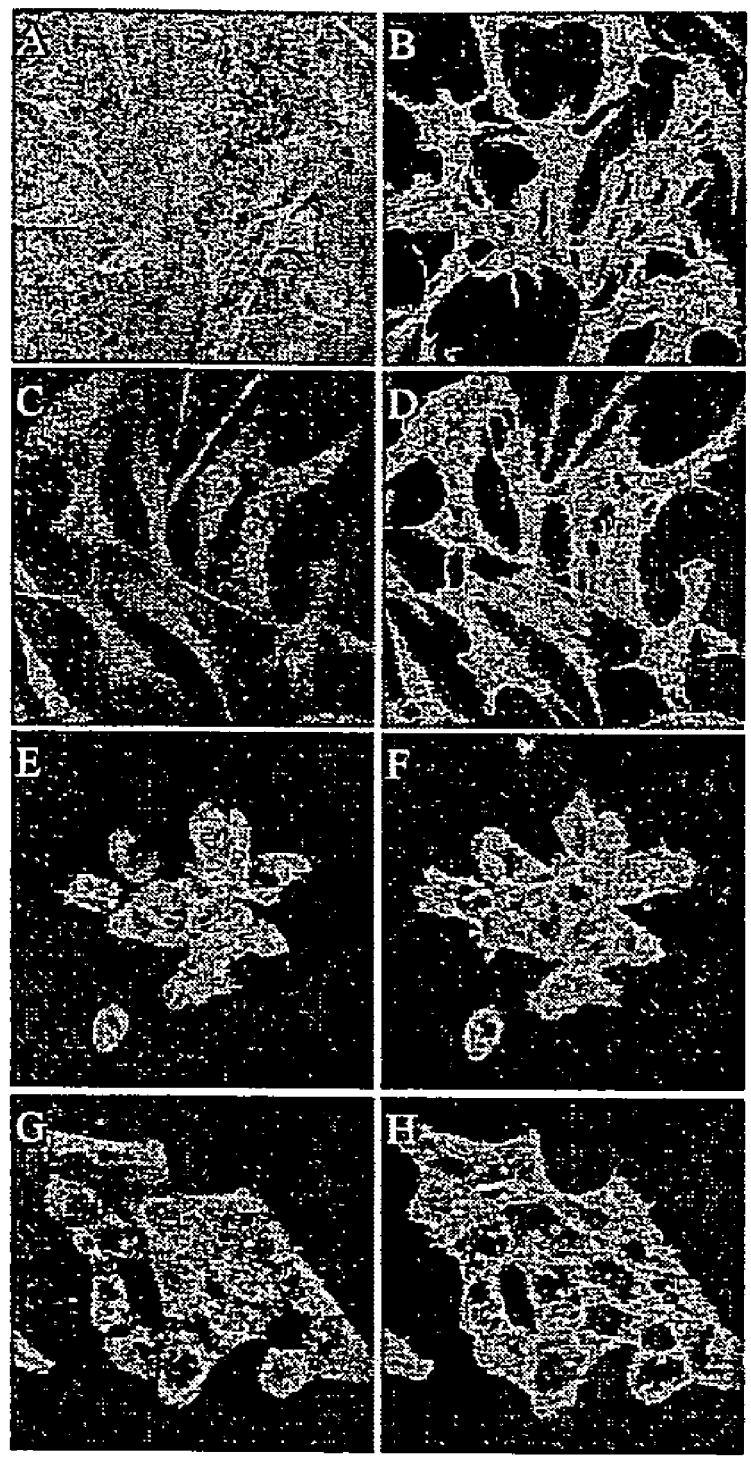
FIG. 4 demonstrates that the anti-Caveolin-1 polyclonal antibody of the present invention can be used to detect the endogenous Caveolin-1 in human A431 cells (A-D) and mouse NIH 3T3 cells (E-H) by immunofluorescence cell staining; wherein the anti-Caveolin-1 polyclonal antibody of the present invention is used to stain the endogenous Caveolin-1 in said cells (A and E), and pre-immune rabbit serum is used as a negative control (C and G). Texas-red-conjugated phalloidin is used for counter stain (B, D, F and H).

Mouse NIH 3T3 cell culture and human A431 cell culture were respectively added on a 22×22 mm cover glass at the concentration of 3×10$^5$ cells/mL, and incubated for 24 hours. The cells were fixed in 4% paraformaldehyde for 15 minutes, then washed in 1× phosphate buffered saline (PBS) 3 times, each time for 5 minutes. 0.5% Triton X-100 was added and kept at room temperature for 10 minutes to permeate the cells, then the cells were again washed in 1×PBS 3 times, each time for 5 minutes. Next, the cells were blocked with 10% normal goat serum (Jackson Immunoresearch Laboratories, USA) in 1×PBS at room temperature for 1 hour, then washed in 1×PBS 3 times, each time for 5 minutes. After that, a 1:300 dilution of the immune serum comprising the polyclonal antibody of the present invention in PBS was applied to the cell-coated cover glass, and kept at 4° C. overnight, the cells were then washed 3 times in 1×PBS, each time for 5 minutes. Subsequently, a 1:300 dilution of FITC-conjugated donkey anti-rabbit IgG secondary antibody (Jackson Immunoresearch Laboratories, USA) was applied to the cover glass, and incubated in the dark for 2 hours, the cells were then washed 3 times in 1×PBS, each time for 5 minutes. The cells were counter-stained by 10 ng/mL Hoechst 33342 (Sigma-Aldrich Fine Chemical, Inc.) and 2.5 μg/mL Texas-red-conjugated phalloidin (Sigma-Aldrich Fine Chemical, Inc.) at room temperature for 10 minutes, and then washed in PBS 3 times. Finally, the stained cells were mounted in mounting medium Mowiol 4-88 (Calbiochem, Germany), sealed with transparent nail polish, and observed under laser scanning confocal microscopy (LSM 510; Zeiss). The cell staining results are shown in FIG. 4. From these results, it is known that the polyclonal antibody of the present invention recognizes Caveolin-1 naturally produced in human and mouse cells.

Immunoprecipitation

Figure 5:
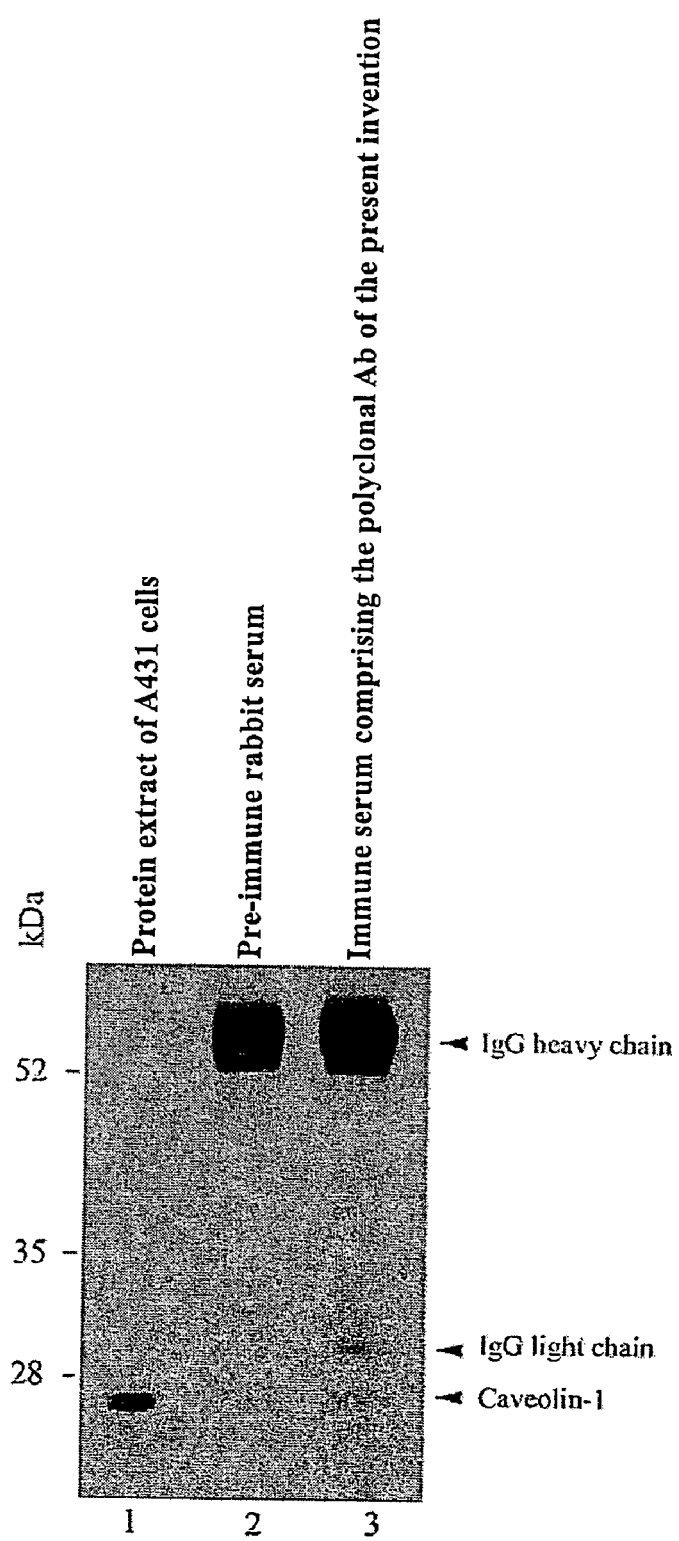
FIG. 5 shows the immunoprecipitation of the protein extract of human A431 cells by the anti-Caveolin-1 polyclonal antibody of the present invention, and demonstrates that the anti-Caveolin-1 polyclonal antibody of the present invention precipitates the endogenous Caveolin-1 in human cells by immunoprecipitation.

Human A431 cell extract was used in an immunoprecipitation test. 500 μL RIPA buffer was added to 3×10$^6$ A431 cells to extract the total protein of the cells, and the concentration of the protein was adjusted to 1 μg/μL. 500 μL of the protein was mixed with 1 μL of pre-immune rabbit serum or the immune serum comprising the polyclonal antibody of the present invention, then rotationally mixed at 4° C. for 30 minutes. 20 μL Protein A-Sepharose slurry was added, then the mixture was rotated at 4° C. for a further 30 minutes. Next, the mixture was centrifuged at 12,000 rpm (15,000 g) for 5 minutes at 4° C. The supernatant from this step was removed and discarded, and the pellet was washed in NET buffer [150 mM NaCl, 1 mM EDTA, 50 mM Tris (pH 8)] 3 times, and centrifuged at 12,000 rpm for 5 minutes at 4° C. after each wash. After the last wash, the supernatant was completely removed, 50 μL 2× Laemmli buffer was added to the pellet and mixed well, and the mixture was heated at 95° C. for 5 minutes. After that, the mixture was centrifuged at 12,000 rpm for 5 minutes at room temperature, and the supernatant was collected as a protein sample to perform Western blotting. The results are shown in FIG. 5. From these results, it is known that the polyclonal antibody of the present invention can successfully immunoprecipitate the endogenous Caveolin-1 in A431 cells.

Since the polyclonal antibody of the present invention can successfully purify the endogenous Caveolin-1 by immunoprecipitation, the position of the antigen peptide sequence that binds the polyclonal antibody of the present invention can be used to confirm whether the antibody produced by said peptide sequence can purify Caveolin-1 by immunoprecipitation or immunoabsorption, or whether it can be used as a co-immunoprecipitation tool to study proteins that interact with Caveolin-1.

Estimation of Caveolin-1 Expression in Biopsy

It is well-known that Caveolin-1 is expressed in normal human breast and colon tissue. Therefore, normal and tumorous human breast tissue (from 25 patients) and colon tissue (from 25 patients) were derived from 50 breast or colon cancer patients, wherein these specimens were obtained from National Taiwan University Hospital. The normal tissue, which was used as a control, was derived from the peripheral region of the tumorous tissue from the corresponding patient.

Figure 6:
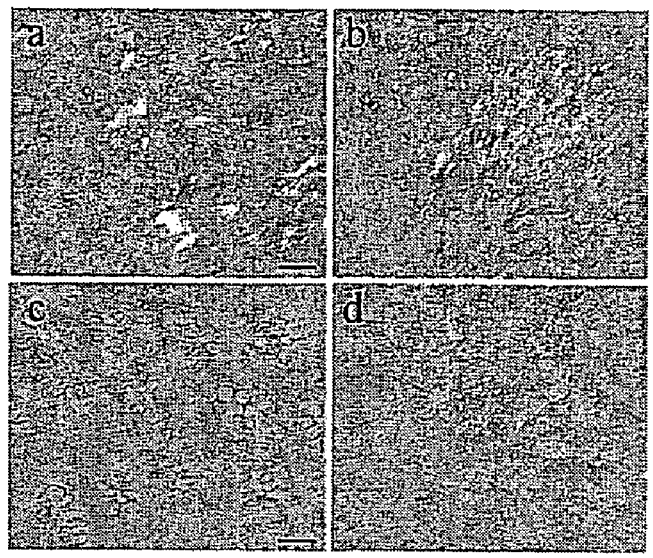
FIG. 6A shows DAB staining of the frozen sections of normal and tumorous human breast or colon tissue obtained from breast or colon cancer patients (a: normal breast tissue; b: tumorous breast tissue; c: normal colon tissue; d: tumorous colon tissue). The expression of Cavelin-1 in tumorous tissues is lower than in normal tissues.
FIG. 6B shows a statistical analysis of the red-brown precipitates in the sections under light microscopy, which are categorized according to formation time and intensity of said precipitates.
Figure 6:
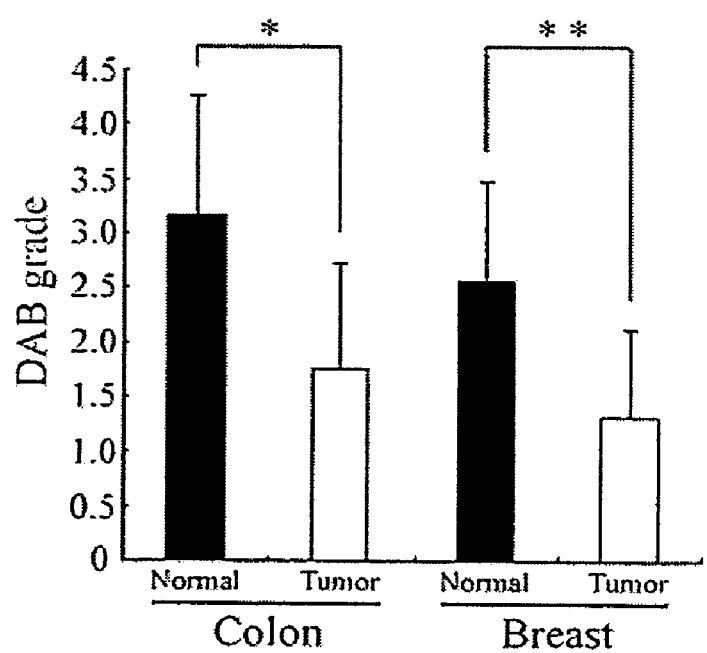

The above-mentioned normal and tumorous human breast or colon tissue was cryo-sectioned into 7 μm-thick sections and fixed with 4% paraformaldehyde, then washed in 1×PBS 3 times, each time for 5 minutes. These sections were then treated with 0.3% H$_2$O$_2$ at room temperature for 30 minutes to inactivate endogenous peroxidase activity, then washed in 1×PBS 3 times, each time for 5 minutes. After that, these sections were blocked in 10% normal goat serum at room temperature for 1 hour, then washed in 1×PBS 3 times, each time for 5 minutes. A 100 μL dilution of the immune serum comprising the polyclonal antibody of the present invention (1:100, in PBS) was added onto the sections in a sealed humid container to hybridize for 12-24 hours, then the sections were washed in 1×PBS 3 times. These treated sections were then soaked in 100 µL dilution of HRP-conjugated anti-rabbit IgG antibody (1:300, in PBS) at room temperature for 2 hours, then the sections were washed in 1×PBS 3 times, each time for 5 minutes. After that, ABC kit (Vectastain Elite), $H_2O_2$ and diaminobenzidine tetrahydrochloride (DAB) reagent were used to form reddish precipitate. The sections were dried, mounted with 90% glycerol/PBS, and sealed by transparent nail polish. The results are shown in FIG. 6A. From these results, it is known that the polyclonal antibody of the present invention can distinguish the difference of the Caveolin-1 expressions between normal and tumorous tissues.

In addition, the reddish precipitate formed in these sections can be categorized into 6 grades by the formation time and the color strength. Statistical analysis by paired t-test (using SAS, version 9.1) confirmed that the polyclonal antibody of the present invention can effectively distinguish between the different levels of Caveolin-1 expression found in normal and tumorous tissues. These results are shown in FIG. 6B. From these results, it is known that the polyclonal antibody of the present invention can be used to distinguish between normal and tumorous tissues of breast or colon, and can be used to monitor the disease progression of breast or colon cancer.

What is claimed is:

1. An isolated anti-Caveolin-1 polyclonal antibody, which is used as a cancer indicator for monitoring cancer progression, wherein said anti-Caveolin-1 polyclonal antibody binds to SEQ ID NO: 1 and is prepared by the following steps:
 i) providing an antigen comprising one or more Caveolin-1 peptides consisting of the sequence SEQ ID NO: 1; and
 ii) subcutaneously injecting said antigen into a rabbit to produce the anti-Caveolin-1 polyclonal antibody.

2. The anti-Caveolin-1 polyclonal antibody according to claim 1, wherein said antigen is of the formula:

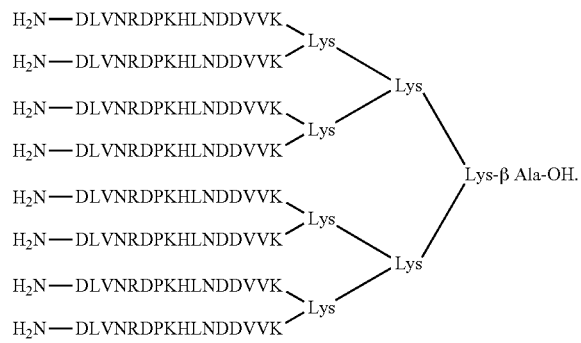

3. The anti-Caveolin-1 polyclonal antibody according to claim 1, wherein said anti-Caveolin-I polyclonal antibody recognizes Caveolin-1 of mammals.

4. The anti-Caveolin-1 polyclonal antibody according to claim 3, wherein said mammals comprise human, cattle, goat, rat or mouse.

5. The anti-Caveolin-1 polyclonal antibody according to claim 1, wherein said cancer comprises breast cancer or colon cancer.

6. A method for preparing an isolated anti-Caveolin-1 polyclonal antibody, comprising the following steps:
 i) providing an antigen comprising one or more Caveolin-1 peptides consisting of sequence SEQ ID NO: 1; and
 ii) subcutaneously injecting said antigen into a rabbit to produce the anti-Caveolin-1 polyclonal antibody.

7. The method according to claim 6, wherein said antigen is of the formula:

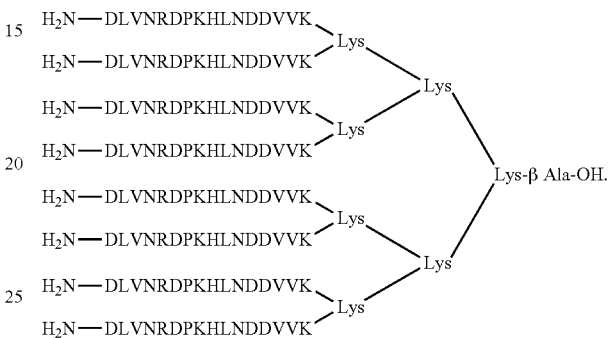

8. A kit used for detecting Caveolin-1 in a specimen, comprising the anti-Caveolin-1 antibody according to claim 1.

9. The kit according to claim 8, further comprising a secondary antibody having a signal.

10. The kit according to claim 9, wherein said signal is fluorescence- or enzyme-generated.

11. The kit according to claim 10, wherein said enzyme is horseradish peroxidase (HRP).

12. The kit according to claim 8, wherein said specimen is a tissue section or a cell sample.

13. The kit according to claim 12, wherein said specimen is a cancer tissue section.

14. The kit according to claim 13, wherein said specimen is a breast cancer or colon cancer tissue section.

15. The kit according to claim 8, wherein said specimen is obtained from human, cattle, goat, rat or mouse.

16. The kit according to claim 8, which is used for detecting Caveolin-1 in a cancer tissue specimen.

17. The kit according to claim 16, wherein said cancer is breast cancer or colon cancer.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Asp Leu Val Asn Arg Asp Pro Lys His Leu Asn Asp Asp Val Val Lys
1               5                   10                  15

<210> SEQ ID NO 2
<211> LENGTH: 135
<212> TYPE: PRT
<213> ORGANISM: Artificial Sequence
<220> FEATURE:
<223> OTHER INFORMATION: Three Dimensional Antigen Synthesized From
      Caveolin-1 Peptide
<220> FEATURE:
<221> NAME/KEY: MISC_FEATURE
<222> LOCATION: (135)..(135)
<223> OTHER INFORMATION: Xaa is a naturally occurring amino acid

<400> SEQUENCE: 2

Asp Leu Val Asn Arg Asp Pro Lys His Leu Asn Asp Asp Val Val Lys
1               5                   10                  15

Asp Leu Val Asn Arg Asp Pro Lys His Leu Asn Asp Asp Val Val Lys
            20                  25                  30

Asp Leu Val Asn Arg Asp Pro Lys His Leu Asn Asp Asp Val Val Lys
        35                  40                  45

Asp Leu Val Asn Arg Asp Pro Lys His Leu Asn Asp Asp Val Val Lys
    50                  55                  60

Asp Leu Val Asn Arg Asp Pro Lys His Leu Asn Asp Asp Val Val Lys
65                  70                  75                  80

Asp Leu Val Asn Arg Asp Pro Lys His Leu Asn Asp Asp Val Val Lys
            85                  90                  95

Asp Leu Val Asn Arg Asp Pro Lys His Leu Asn Asp Asp Val Val Lys
            100                 105                 110

Asp Leu Val Asn Arg Asp Pro Lys His Leu Asn Asp Asp Val Val Lys
        115                 120                 125

Lys Lys Lys Lys Lys Lys Xaa
    130                 135

<210> SEQ ID NO 3
<211> LENGTH: 27
<212> TYPE: DNA
<213> ORGANISM: Artificial Sequence
<220> FEATURE:
<223> OTHER INFORMATION: Primer
```

-continued

```
<400> SEQUENCE: 3
ctcgagatgt ctgggggcaa atacgtg                                          27

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
tctagatatc tctttctgcg tgctgatgcg                                       30

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gaattcggta ccatggggct ggagaccgag aaggc                                 35

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
aagctttcta gagtcgtggc tcagttgcat gc                                    32

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
cggcagcggc acgagtc                                                     17

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ctcccgcacc aagttttccc atct                                             24

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ggatccctcg agatgatgac cgaagagcac acgg                                  34

<210> SEQ ID NO 10
<211> LENGTH: 34
<212> TYPE: DNA
```

-continued

```
<213> ORGANISM: Artificial Sequence
<220> FEATURE:
<223> OTHER INFORMATION: Primer

<400> SEQUENCE: 10
aagctttcta gagccttccc ttcgcagcac cacc                    34
```